United States Patent [19]

Olson

[11] 4,251,507

[45] Feb. 17, 1981

[54] PROCESS AND COMPOSITION FOR REDUCING DENTAL PLAQUE

[75] Inventor: B. Newell Olson, Norwich, N.Y.

[73] Assignee: Dominion Pharmacal, Inc., Norwich, N.Y.

[21] Appl. No.: 81,045

[22] Filed: Oct. 2, 1979

Related U.S. Application Data

[63] Continuation-in-part of Ser. No. 858,298, Dec. 7, 1977, abandoned.

[51] Int. Cl.³ .................. A61K 7/16; A61K 7/18; A61K 31/79; A61K 47/00
[52] U.S. Cl. .................. 424/49; 424/50; 424/51; 424/52; 424/53; 424/54; 424/55; 424/56; 424/57; 424/80; 424/362
[58] Field of Search ................ 424/49–58, 424/80, 362

[56] References Cited

U.S. PATENT DOCUMENTS

| | | | |
|---|---|---|---|
| 2,751,328 | 6/1956 | Sanders | 424/49 |
| 3,914,406 | 11/1975 | Yankell | 424/52 |
| 3,932,605 | 1/1976 | Vit | 424/49 |
| 3,932,607 | 1/1976 | Hesselgren | 424/49 |
| 3,937,807 | 2/1976 | Haefele | 424/49 |
| 3,940,476 | 2/1976 | Haas | 424/49 |
| 3,954,962 | 5/1976 | Prussin | 424/49 |
| 3,966,901 | 6/1976 | Cullum et al. | 424/49 |
| 4,067,962 | 1/1978 | Juneja | 424/49 |
| 4,071,614 | 1/1978 | Grimm | 424/49 |

*Primary Examiner*—Douglas W. Robinson

[57] ABSTRACT

The present invention relates to an improved method for cleansing of human teeth to help reduce and control dental plaque as an aid in preventing dental caries and periodontal disease. In particular, it relates to a viscous composition of particular characteristics and a process for application thereof to accomplish these objectives.

3 Claims, No Drawings

PROCESS AND COMPOSITION FOR REDUCING DENTAL PLAQUE

This application is continuation-in-part of Ser. No. 858,298, Dec. 7, 1977; Abandoned.

BACKGROUND OF THE INVENTION

Incidence of dental caries and periodontal disease has been linked in the technical literature to plaque on teeth. Numerous references treat the subject of dental plaque adequately. One such reference is "Dental Pathology and Therapeutics" by Henry H. Burchard, M.D., Fifth Edition published by Lea and Febiger, Philadelphia, USA, 1915. Dental plaque is known to comprise a thin coating of a mucilaginous and gelatinoid-type material on teeth which can be invaded by colonizing bacteria. "Microbic" plaque is the term often used to describe this condition after colonization has occurred. Metabolic activity of these bacteria within the plaque in presence of dietary carbohydrate, for example, can lead to production of various acids such as acetic, butyric and lactic. These acids may attack, not only soft gum tissue, but are believed to react with calcium of the teeth leading to tooth decalification through formation of calcium salts. Such decalification can expose organic matrix of the tooth, i.e., dentin allowing for further invasion by bacteria and liquifying enzymes. Because tooth structure includes tubules radiating outward from sensitive tooth pulp, deep penetration into teeth is often V-shaped and can occur within a short time period after hard surface enamel has been broken down. Other explanations have also been offered in the technical literature as to the mechanism of formation of dental caries and periodontal disorders. However, medical opinion seems fairly united in that plaque is one primary cause of these problems and that reduction and control of dental plaque are essential to sound oral hygiene.

Attempts have been made in the past to prevent dental caries by a number of means. These include, for example, fluoridization of drinking water in an effort to harden tooth enamel. Data gathered from areas where fluoridization is being carried out show that incidence of dental caries is considerably reduced in such areas. Other efforts to help prevent dental caries include the use of inorganic fluorides in tooth pastes, mouth rinses, tooth powders, lozenges, dental creams, chewing gum tablets and the like. In other applications, efforts have been made to help prevent gingivitis which is the most common precursor of periodontal disease. Gingivitis is defined as a reddening and swelling of the normally pink gums and may be accompanied by occasional bleeding. This inflammation is often progressive leading to ulceration of the gums and final destructive effect on supporting fibers and bone which anchor the teeth. Various processes and compositions for helping prevent dental caries and periodontal disease are described in U.S. Pat. Nos. 3,932,607; 3,914,406; 2,818,371 and 2,913,373.

In other attempts to reduce and control dental plaque, various anti-microbial agents and organic fluorides have been recommended for use. Typical compounds of these types are described in U.S. Pat. Nos. 3,954,476 and 4,067,962. In another U.S. patent, namely U.S. Pat. No. 3,954,962, a combination of ingredients is described for use in a special type tooth paste which is applied to a toothbrush and then used in conventional manner. This combination comprises a non-aqueous, alcohol-based combination incorporating polyvinylpyrrolidone resin and glycerine. Topical application of various compounds to the teeth is described in U.S. Pat. No. 3,940,476. In this approach, attempt is made to prevent formation of plaque by inhibiting growth of cariogenic bacteria. While this approach can be expected to have some beneficial effect, the heavy activity of flora of the mouth would be expected to over-ride any inhibiting action unless the frequency and degree of usage of such agents would lead to a sterile condition within the oral cavity. If this were to occur deleterious effects on delicate mucous membranes would seem likely as would a loss of natural balance of gram-positive and gram-negative bacteria within the normal flora of the mouth.

From a review of these patents and other information in the literature, it is apparent that an improved means to help prevent dental caries and periodontal disease is still badly needed. From a reading of information in the art it is obvious that the basic need is not satisfied since the cause of dental caries and periodontal disease is considered to be plaque on the teeth as hereinbefore indicated. None of the means presently available appear to get at the heart of this problem which is finding an improved means for cleansing of human teeth so that plaque can be reduced and controlled. It is apparent that no known means is now available which can accomplish this on a totally safe and effective basis. Inasmuch as mouth washes and mouth rinses are well known to lack effectiveness as a means to cleanse plaque from human teeth, there appears to be very little available to serve to effectively accomplish this purpose. The present invention, however, has now very unexpectedly found an improved means for reducing and controlling plaque on human teeth without the need to introduce toxic or dangerous materials into the mouth. In addition, the present invention gets at the heart of the problem by providing a safe and improved means for reducing and controlling plaque by application of a cleansing process that effectively cleanses plaque from human teeth as an aid in preventing dental caries and periodontal disease. Also, and very significantly, the present invention can be used safely by the general public, children and adults alike, without the need for specialized instruction. Moreover, the present invention requires no special prescription or dispensing by professionals or physicians. Thus, it provides basis for new and significant products which can be entered into the commercial mainstream without delay to aid in the acute need to help prevent dental caries and periodontal disease.

SUMMARY OF THE INVENTION

It is an object of this invention to provide an improved means for cleansing of human teeth.

It is a further object of this invention to provide an improved means for reducing and controlling dental plaque.

It is a still further object to provide an improved means for helping prevent dental caries and periodontal disease.

It is still another object to provide a means for delivery of widely varied ingredients to human teeth in a manner that effects improved cleansing and/or deposition thereto of such ingredients.

It is a still further object to provide a means for reducing and controlling plaque on human teeth which will be adaptable for use by individuals without reliance on professionally trained persons to administer application thereof.

Another object of this invention is to provide a means for reducing and controlling plaque on human teeth which will be sufficiently safe and easy to use so as to be readily available and not limited to dispensing by prescription only.

Apart from the compositions and techniques described in the prior art and the patents herein enumerated, the present invention takes from the art of photographic diffusion transfer and continuous photographic development technology and makes application to dental plaque in the oral cavity. Photographic diffusion transfer is well known in the photographic arts. It is described in numerous U.S. patents such as U.S. Pat. No. 3,265,458. It involves the transfer of metal halides from one stratum to another when dissimilar stratums are placed in contiguous contact. Numerous patents have issued on this technology due in part to the unexpectedness with which such transfer takes place. The speed of such transfer has brought to fruition the recent innovation of "instant" photography. In this field, viscous compositions are described for application in effecting diffusion transfer. One such application is described in U.S. Pat. No. 3,238,043. While it is well known that silver halides such as silver bromide, chloride and iodide are involved in these photographic processes, silver fluorides are not normally mentioned.

In another method of application, the technology of diffusion transfer can be observed in modern day television commercials. These commercials relate to advertisements for proper use of liquid detergents in cleansing "ring around the collar" from men's shirts. As these ads graphically illustrate, the detergent should be applied directly to the "ring" and not to the wash water. Quite obviously, by applying cleansing ingredients directly to the "ring", ease of removal of the ring from the shirt is enhanced. As diffusion transfer technology dictates, contiguous contact markedly accelerates transfer of ingredients from one stratum to another.

In accordance with the present invention, a means was desired for helping prevent dental caries and periodontal disease. To accomplish this an improved means was needed to reduce and control dental plaque known to be a significant causative factor. The most expedient means to accomplish this would seem to be to find an improved means for cleansing human teeth so that plaque could be effectively removed. Based on information from diffusion transfer technology, it would appear that effectiveness of any product for use in this application would depend upon its ability to transfer cleansing ingredients into the plaque so as to assist in its ready removal. Based on tests conducted it has now been found, quite unexpectedly, that transfer of cleansing ingredients to plaque on human teeth does occur from a viscous composition of this invention such that dental plaque can be effectively removed and thereby reduced and controlled. While not wanting to be bound by any technical limitations thereof, and for purposes of illustration only, the inventor suggests that improved cleansing of human teeth in accordance with the invention is by way of diffusion transfer technology as herein described.

For reasons of oral hygiene as enumerated above, a means for improving cleansing of human teeth beyond that available through conventional products and practices is badly needed. From a review of human teeth after regular care with conventional products where dye tablets are used to show evidence of plaque still remaining on the teeth, it is apparent that the greatest deposits remain at or near the gum line and medianly at the interface between the teeth. Clearly, conventional care practices including toothpastes and brushing do not effectively reach these areas to remove plaque from them. Therefore, if reduction in dental caries and periodontal disease is to be realized, an improved means for cleansing human teeth in these vital areas is needed.

DESCRIPTION OF PREFERRED EMBODIMENTS

In a preferred embodiment of the invention, a composition is prepared according to examples contained herein. This composition is then placed in a compressible package equipped with an elongated member having an orifice at the distal end wherein said member is of sufficient length to extend from said compressible package to the most remote teeth within the oral cavity. In the process of this invention, the elongated member is inserted into the oral cavity between gum and cheek in such a manner that the orifice at the distal end of the elongated member is positioned adjacent the molar having the highest number such as the third molar. The orifice is positioned on the buccal side of said molar in a position proximate to the interface of tooth and gum. Gentle squeezing action is then applied to the compressible package by pressure between thumb and index finger such that a thin line or bead of viscous composition is extruded from said orifice onto said molar. The orifice is then drawn slowly forward and circumferentially within the oral cavity until the buccal and labial sides of all teeth have a thin bead of viscous composition extruded thereon. The bead is then allowed to remain in position for a period of time from about 10 seconds to about 30 seconds. Due to special viscosity inducing ingredients in the composition, at body temperature, the bead begins to spread over the surface of the teeth and between the teeth. Within the time period specified, the composition effectively spreads over the surface of the teeth and between the teeth so as to come into direct contiguous contact with plaque contained thereon. It will be apparent that the composition importantly, must facilitate spreading over tooth surface while retaining sufficient integrity in the presence of salivary juices to avoid being washed away even when spread over the tooth's surfaces as a very thin film.

After allowing the prescribed time period to elapse after application of the bead from the compressible package, the teeth are brushed with a dry or moistened toothbrush. The brushing is carried out by an appropriate number of upward, downward, forward, backward and circumferential strokes typical of tooth brushing activity. Following brushing, the oral cavity can be rinsed with water as desired.

The composition of this invention contains as an essential ingredient, a water soluble, viscosity-inducing ingredient having the capacity to fuse at body temperature and spread evenly over a wet surface within limited time period while maintaining sufficient physical integrity of composition to avoid washing away in the presence of salivary juices. Compounds having these characteristics according to the invention can be selected from the class comprising cellulosic deriviatives. While compounds suitable for use in the invention can be selected from those comprising methyl celluloses, ethyl celluloses and carboxy celluloses, it has been found that the preferred class of compounds comprise those referred to as low molecular weight, cold water soluble, partially hydrolyzed cellulose ethers. Particular members within this group comprise methyl cellulose, hydroxy propyl cellulose, hydroxy propyl methyl cellulose and hydroxy propyl butyl cellulose such as those available from the Dow Chemical Company under the trade name of "Methocel". Within the selection of a particular type cellulosic compound, the viscosity of that compound in aqueous solution is very important. It has been found for example, that cellulosic members having a physical viscosity in the range of from about 1500 to about 15,000 centipoises are preferred. An even more preferred viscosity is in the range from about 1,800 to about 12,000. A still more preferred viscosity has been found to be in the range of from about 3,500 to about 5,600. In this determination, viscosity is measured in centipoises using a 2 percent aqueous solution at a temperature of 20 degrees centigrade following detailed procedures as given in A.S.T.M. Standards D 1347-72 and D 2363-72.

The compositions of this invention can contain additional ingredients such as detergents, fluorides, flavorings, sweetening agents, colorants, humectants, stabilizers, solubilizers and anti-microbial agents. Typical materials of these kinds are well known in the art and can be seen in such U.S. patents as U.S. Pat. No. 4,067,962. Typical detergents comprise sodium lauryl sulfate, ammonium lauryl sulfate, magnesium lauryl sulfate, sodium lauryl sulfoacetate and sodium lauryl sarcosinate. Typical fluorides include sodium fluoride, potassium fluoride, stannous fluoride, potassium stannous fluoride, sodium hexafluorostannate, stannous chlorofluoride, sodium monofluorophosphate and the like. These compounds are known to release fluorine-containing ions in water and should be present in an effective but safe range in terms of water-soluble fluorine content. Typical flavorings comprise cosmetically acceptable flavors and flavoring agents. Suitable materials for this purpose are well known in the flavoring art and can be selected from a broad list. Suitable ones can include flavoring oils, e.g., oil of spearmint, peppermint, wintergreen and other flavoring compounds such as clove, sage, eucalyptas, cinnamon, lemon, etc. Typical sweetening agents for use in the invention include sodium saccharin, sodium cyclamate, sorbitol and the like.

Suitable colorants for use in the invention comprise those referred to in the trade as FD&C colorants as provided by a number of U.S. suppliers. Typical humectants for use in the invention comprise glycerine, sorbitol and other suitable polyhydric alcohols and mixtures thereof. Typical stabilizers and or solubilizers for use in the invention can comprise water-soluble non-ionic surface active agents such as condensates of sorbitan monosterarate with from 20 to 60 moles of ethylene oxide such as the "Tween" compounds available from ICI United States, Inc.; condensates of propylene glycol and polyoxyethylene such as the "Pluronics" available from BASF Wyandotte Corporation; fatty alcohol ethoxylates such as the "Siponic" compounds available from Alcolac, Inc. and the like. In a preferred embodiment, the ideal non-ionic surfactant is selected on the basis of its low surface tension, cleansing ability, freedom from off-taste and stability over extended periods of time.

Typical anti-microbic agents for use in this invention comprise those having an anti-bacterial effectiveness in dilute concentration against a wide range of both gram-positive and gram-negative organisms. These can be selected from the class comprising alkyl halide derivatives of quaternary ammonium compounds such as diisobutylphenoxyethoxyethyldimethylbenzyl ammonium chloride, alkyldimethylbenzyl ammonium chloride, diisobutylcresoxyethoxyethyldimethylbenzyl ammonium chloride, alkyltrimethyl ammonium chloride, carboxypentadecyltrimethyl ammonium chloride and phenoxyethyldimethyldodecyl ammonium chloride.

The instant compositions normally have a pH between 5 and 9 and preferably in the range of from 6 to about 8. Suitably, a buffering system may be employed to assure maintenance of pH within the desired range. Typically, aqueous solutions of acid salts may be advantageously employed for this purpose.

When compositions of this invention are applied to human teeth within the process of this invention as prescribed previously, highly desirable improved cleansing is effected. For purposes of clinical proof of this result, human subjects can be used within widely varied age groupings. Since the compositions and process are safe, both children and adults alike can be used in any determination to provide evidence of clinical effectiveness. In addition such a determination can be made on a simplistic basis since only a direct comparison need be made against comparative cleansing effectiveness where conventional toothpaste and brushing procedures are used. Preferably, each subject in such an effectiveness test should be given a pre-examination to assure freedom from dental caries, gingivitis, ulcerations and other oral pathology. Each subject should then be given an arbitrary score as to degree of plaque present on each tooth of the oral cavity. Quite appropriately, dye tablets, in chewable form, are available as over-the-counter products at many drug stores which can be used in this scoring process. After utilization of the chewable tablets, each tooth can be given a gross visual examination to determine degree of plaque. The score applied to each tooth can then be used at the end of the test to ascertain the amount of reduction in plaque on each tooth in each of the test subjects. Subjects having comparable degree of plaque at the start of the test are paired wherein one subject cleanses his or her teeth in conventional manner using a toothpaste and tooth brush of choice. The other subject then cleanses his or her teeth with comparable frequency and duration of brushing except that composition and process of the present invention are used. Reduction in plaque score at the end of the test period in comparison to the plaque score of matched subjects in the comparative group is an indication of reduction of plaque and hence improved cleansing of human teeth due to the composition and process of this invention.

In accordance with the invention, it has been found that the compositions and process are high effective in securing the desired effect of improved cleansing of human teeth and that this result can be obtained with complete safety when following simple instructions. This desired result can easily be obtained by individuals without required treatment by specialized persons, such as dentists, nurses and hygienists. Accordingly, this invention constitutes a significant advance in the field of dental prophylactic effect available to great numbers of persons. Moreover, since the process and compositions involve no pronounced risk or hazard to the user, products marketed under this application can be sold without the need for a prescription from a dentist or physician.

The following specific examples are further illustrative of the present invention but it is to be understood that the invention is not limited thereto. Unless otherwise specified, the amounts and proportions in each of the examples are by weight.

EXAMPLE I

| Viscous Cleansing Composition | | |
|---|---|---|
| Ingredients | | Amounts |
| Part A: | | |
| 1. | Water (85° C.) | 15.00% |
| 2. | Hydroxy propyl methyl cellulose (4000 Centipoises) | 1.85% |
| 3. | Water (16-20° C.) | 52.30% |
| Part B: | | |
| 4. | Water (55° C.) | 10.00% |
| 5. | Sodium lauryl sulfate | 5.00% |
| 6. | Methylparaben | 0.20% |
| 7. | Propylparaben | 0.20% |
| 8. | Flavoring | 1.00% |
| 9. | Flavoring solubilizer | 1.65% |
| 10. | Sorbitol | 5.00% |
| 11. | Sodium saccharin | 0.20% |
| 12. | FD&C Blue #1 | q.s. |
| 13. | FD&C Yellow #5 | q.s. |
| 14. | Water sufficient to make | 100.00% |

In a manner of preparing the composition of this example, hydroxy propyl methyl cellulose powder is added to pre-heated water of Part A and stirred to obtain a uniform dispersion. Cold water at 16°–20° C. is then added with stirring to effect solubilizing of the cellulose. Part A is then set aside for later addition to Part B.

Part B is prepared by adding sequentially, with stirring, each of the ingredients shown except that ingredients 8 and 9 are pre-mixed before addition to the batch. Slow, steady stirring is maintained throughout the preparation process. Part A is then added, with stirring, to Part B to complete the composition.

In a manner of application, the composition is then drawn into a compressible plastic package equipped with an elongated nozzle of sufficient length to reach the region of the third molar within the oral cavity while the compressible package is positioned at the labial exterior of the mouth. To effect application of the contents to human teeth, the distal end of the elongated nozzle is positioned at interface of tooth and gum in the third molar region. While exerting slight digital pressure onto the compressible package such that extrusion of composition is effected from the nozzle, the nozzle is drawn slowly forward and circumferencially within the oral cavity until a thin bead of composition is extruded at interface of tooth and gum of all teeth within the oral cavity. After allowing from about 10 to about 30 seconds for the composition to spread evenly over the surface of each tooth and between the teeth, a toothbrush, preferably moistened with water but having no other composition thereupon, is used to brush the teeth in regular manner. Such brushing should include normal brushing technique, i.e., utilizing varied forward, backward, downward and circumferential strokes to effect cleansing of the teeth. Following this, the contents of the oral cavity are expelled and the mouth can be rinsed with water as desired.

It will be apparent that numerous ingredients can be substituted within the composition of Part B of Example I. These are described hereinabove and are well known in the trade and are readily available from a review of appropriate literature.

Within Part A, however, restrictive limits are involved. These include use of a cellulose derivative having viscosity-inducing properties, smooth spreading capability at body temperature and ability to withstand washing away from tooth surfaces in the presence of salivary secretions. Typical among this group are cellulose derivatives having a viscosity in the ranges specified above. In the manner of preparation of Example I, the use of hydroxy propyl methyl cellulose available from Dow Chemical Company and designated as "Methocel F4M" is a typical example.

EXAMPLE II

| Viscous Cleansing Composition with Fluoride | | |
|---|---|---|
| | Ingredients | Amounts |
| 1. | Water (85° C.) | 15.00% |
| 2. | Methyl cellulose | 2.35% |
| 3. | Water (16-20° C.) | 47.00% |
| 4. | Ammonium lauryl sulfate | 3.00% |
| 5. | Tween 60 | 2.00% |
| 6. | Flavoring | 0.85% |
| 7. | Flavoring solubilizer | 1.00% |
| 8. | Glycerine | 9.00% |
| 9. | Sodium fluoride | 0.50% |
| 10. | Sodium saccharin | 0.20% |
| 11. | Distilled water to make | 100.00% |

Ingredients 1, 2 and 3 are prepared as in Example I and then placed in a mixing vessel. All remaining ingredients are then added in order of appearance except that ingredients 6 and 7 are pre-mixed prior to addition to batch tank. Continuous slow mixing is maintained within the batch tank during preparation period.

The composition is then used in manner of application described in Example I.

EXAMPLE III

| Viscous Cleansing Composition with Anti-microbic Agent | | |
|---|---|---|
| | Ingredients | Amounts |
| 1. | Water (85° C.) | 15.00% |
| 2. | Hydroxy butyl methyl cellulose (15,000 centipoises) | 1.40% |
| 3. | Water (16-20° C.) | 47.50% |
| 4. | Sodium lauryl sarcosinate | 4.50% |
| 5. | Propylparaben | 0.20% |
| 6. | Pluronic F-108 | 2.00% |
| 7. | Flavoring | 0.80% |
| 8. | Flavoring solubilizer | 1.00% |
| 9. | Propylene glycol | 5.00% |
| 10. | Diisobutylphenoxyethoxyethyldimethylbenzyl ammonium chloride | 0.10% |
| 11. | Sodium saccharin | 0.20% |
| 12. | FD&C Blue #1 | q.s. |
| 13. | Water to make | 100.00% |

The composition of this example is prepared according to the procedure of Example I except that ingredients 7 and 8 as well as ingredients 9 and 10 are pre-mixed prior to addition to the mixing tank.

The composition is then used to cleanse human teeth according to the procedure of Example I.

EXAMPLE IV

| | Viscous Cleansing Composition having fluoride and Anti- Microbic Agent | |
|---|---|---|
| | Ingredients | Amounts |
| 1. | Water (85° C.) | 15.00% |
| 2. | Stannous Fluoride | 0.67% |
| 3. | Hydroxy propyl methyl cellulose (4,000 centipoises) | 1.80% |
| 4. | Water (16-20° C.) | 50.00% |
| 5. | Sodium lauryl sulfate | 4.00% |
| 6. | Propylparaben | 0.20% |
| 7. | Flavoring | 1.00% |
| 8. | Flavoring solubilizer | 2.00% |
| 9. | Propylene glycol | 5.00% |
| 10. | Diisobutylphenoxyethoxyethyldimethylbenzyl Ammonium chloride | 0.10% |
| 11. | Sorbitol | 5.00% |
| 12. | Sodium saccharin | 0.20% |
| 13. | FD&C Blue #1 | q.s. |
| 14. | Water to make | 100.00% |

To prepare the composition of this example, the procedure of Example I is used except that ingredients 1 and 2; 7 and 8; and 9 and 10 are pre-mixed prior to addition to the mixing vessel.

The composition is then used according to the procedure outlined in Example I.

In the practice of this invention, the viscosity and physical characteristics of the various cleansing compositions are very important regarding ability to form and maintain a thin film on human teeth in the presence of body heat and salivary secretions. Viscosity can be measured by any one of a number of methods well known in the art. These include the so-called rolling ball technique where composition is placed in a hollow, elongated cylinder equipped with a steel ball and timing device. In this method, the time required for the ball to roll from one end of the cylinder to the other is taken as a measure of viscosity. Other methods of viscosity measurement are shown in the Encyclopedia of Polymer Science and Technology page 504, Interscience, John Wiley and Sons, New York and London 1965. The method described in that publication is referred to as "Intrinsic Viscosity". The preferred method of viscosity measurement as used herein is described in ASTM Monographs D-1347-72 and D-2363-72. These monographs measure viscosity in terms of centipoises (cps). In the present invention, it was found that centipoise viscosity of the composition measured at 20 degrees centigrade according to methods described in these ASTM monographs provided a reliable measure of acceptable performance in actual use of the compositions. Preferred viscosity range for final compositions of this invention has been hereinbefore enumerated.

The foregoing detailed description has been given for purposes of explaining and illustrating the invention. It is to be understood that the invention is not limited to detailed information set forth, and that various modifications can be made within each example herein provided without departing from the scope of the invention as defined by the appended claims.

What I claim is:

1. In the process of cleansing human teeth within the oral cavity for the purpose of effecting improved means for digital removal of plaque therefrom, the essential steps of (1) extruding directly to the surface of said teeth a thin bead of viscous cleansing composition in which said bead is extruded at the interface of tooth and gum from the orifice of a compressible member by digital pressure applied thereto wherein said extrusion is made circumferentially to the buccal and labial surface of all teeth within the oral cavity wherein said member being of sufficient length to reach the region of the third molar within the oral cavity while said member is positioned at the labial exterior of the mouth, said composition containing therein as essential ingredient thereof a cellulosic derivative selected from the group consisting of methyl cellulose, hydroxy propyl methyl cellulose and hydroxy butyl methyl cellulose wherein said composition spreads over the surface of said teeth within a time period of from about 10 seconds to about 30 seconds without washing away of said composition from the surface of said teeth by salivary juices, and (2) brushing of said teeth with a standard toothbrush having no organic composition thereon using forward, backward, downward and circumferential strokes over said teeth with said toothbrush to effect improved removal of plaque therefrom.

2. In the process of claim 1 in which the cellulosic derivative selected from the group consisting of methyl cellulose, hydroxy propyl methyl cellulose and hydroxy butyl methyl cellulose is present in the composition in an amount from 1% to about 2.5% wherein said cellulosic derivative has a viscosity at 20 degrees centigrade in 2% aqueous solution of from about 1,500 centipoises to about 15,000 centipoises.

3. In the process of claim 2 in which the cellulosic derivative consists of hydroxy propyl methyl cellulose having a viscosity in 2% aqueous solution at 20 degrees centigrade of from 5,000 to 10,000 centipoises and being present in said composition in amount from 1% to 1.5%.

* * * * *